US010668271B2

(12) United States Patent
Buss et al.

(10) Patent No.: US 10,668,271 B2
(45) Date of Patent: Jun. 2, 2020

(54) LEAD STABILIZER FOR DEEP BRAIN STIMULATION

(71) Applicant: OsteoMed LLC, Addison, TX (US)

(72) Inventors: Brian A. Buss, Dallas, TX (US); Kris Smith, Phoenix, AZ (US)

( * ) Notice: Subject to any disclaimer, the term of this patent is extended or adjusted under 35 U.S.C. 154(b) by 305 days.

(21) Appl. No.: 15/715,895

(22) Filed: Sep. 26, 2017

(65) Prior Publication Data

US 2019/0091468 A1    Mar. 28, 2019

(51) Int. Cl.
| | |
|---|---|
| A61N 1/05 | (2006.01) |
| A61B 90/50 | (2016.01) |
| A61B 17/34 | (2006.01) |
| A61B 90/11 | (2016.01) |
| A61B 90/10 | (2016.01) |
| A61M 25/02 | (2006.01) |

(52) U.S. Cl.
CPC ............ *A61N 1/0534* (2013.01); *A61B 90/50* (2016.02); *A61N 1/0539* (2013.01); *A61B 17/3468* (2013.01); *A61B 90/11* (2016.02); *A61B 2090/103* (2016.02); *A61M 25/02* (2013.01); *A61M 2025/024* (2013.01); *A61M 2025/028* (2013.01); *A61M 2025/0213* (2013.01); *A61M 2025/0286* (2013.01); *A61N 1/0558* (2013.01)

(58) Field of Classification Search
CPC .. A61N 1/0539; A61N 1/0534; A61N 1/0531; A61N 1/36082; A61N 1/36067; A61N 1/36017; A61N 1/0529
See application file for complete search history.

(56) References Cited

U.S. PATENT DOCUMENTS

| | | | |
|---|---|---|---|
| 5,843,150 A | 12/1998 | Dreessen et al. | |
| 5,927,277 A | 7/1999 | Baudino et al. | |
| 6,134,477 A * | 10/2000 | Knuteson | A61M 25/02 |
| | | | 607/115 |

(Continued)

FOREIGN PATENT DOCUMENTS

WO    WO-2009/067323 A1    5/2009

OTHER PUBLICATIONS

International Search Report and Written Opinion issued for PCT/US2018/048328; dated Oct. 18, 2018; 14 pages.

*Primary Examiner* — John R Downey
(74) *Attorney, Agent, or Firm* — Norton Rose Fulbright US LLP

(57) ABSTRACT

A surgically implanted lead stabilizer used to stabilize leads is described herein. A lead stabilizer may include a plate that is permanently or semi-permanently surgically installed on a patient's skull under their skin via screws. The plate may hold one or more lead in place. In further embodiments, the plate has two hinged halves that may be affixed fully closed or may include a slotted arm allowing the two hinged halves to be affixed partially open. The plate may include apertures through which electrical leads may pass. Example leads may be guided through one or more surface channels on the top surface of the plate causing the leads to lay flat along the patient's skull. In an example use, a burr hole may be formed in a patient's skull with one or more leads threaded therethrough; a surgeon may open a hinged half of a plate and clamp one or more leads within one or more of the lead holes of the plate, close the hinged halves partially or entirely, affix the plate to the skull, and snap the leads into the surface channels.

21 Claims, 4 Drawing Sheets

(56) References Cited

U.S. PATENT DOCUMENTS

| | | | |
|---|---|---|---|
| 7,704,260 B2 * | 4/2010 | Skakoon | A61B 5/6864 |
| | | | 606/130 |
| 7,766,922 B1 | 8/2010 | Daglow et al. | |
| 7,787,960 B2 | 8/2010 | Lubenow et al. | |
| 7,887,550 B2 | 2/2011 | Daglow et al. | |
| 8,038,685 B2 | 10/2011 | Bedenbaugh | |
| 8,043,304 B2 | 10/2011 | Barker | |
| 8,050,772 B1 | 11/2011 | Daglow et al. | |
| 8,262,674 B2 | 9/2012 | Daglow et al. | |
| 8,315,714 B2 | 11/2012 | Daglow et al. | |
| 8,500,752 B2 | 8/2013 | Bedenbaugh | |
| 8,731,686 B2 | 5/2014 | Lane et al. | |
| 9,043,000 B2 | 5/2015 | Lane et al. | |
| 9,101,756 B1 | 8/2015 | Pianca et al. | |
| 9,457,180 B2 | 10/2016 | Bucholz | |
| 9,539,421 B2 | 1/2017 | Bonde et al. | |
| 9,604,052 B2 | 3/2017 | Behymer et al. | |
| 9,610,437 B2 | 4/2017 | Okun et al. | |
| 2005/0182424 A1 * | 8/2005 | Schulte | A61N 1/0539 |
| | | | 606/130 |
| 2009/0112327 A1 | 4/2009 | Lane et al. | |
| 2010/0179563 A1 | 7/2010 | Skakoon et al. | |
| 2011/0034981 A1 | 2/2011 | Schulte et al. | |
| 2013/0197472 A1 | 8/2013 | Skakoon et al. | |
| 2014/0074202 A1 | 3/2014 | Bedenbaugh | |
| 2014/0135589 A1 * | 5/2014 | Osorio | A61B 5/6868 |
| | | | 600/301 |
| 2016/0143664 A1 * | 5/2016 | Garcia | A61B 17/688 |
| | | | 606/70 |

\* cited by examiner

LEAD STABILIZER FOR DEEP BRAIN STIMULATION

FIELD OF THE INVENTION

This application relates to an adaptable lead stabilizer that is capable of stabilizing one or more leads of various sizes (e.g., unpredictable sizes) extending from one or more burr hole.

BACKGROUND

Brain syndromes/diseases (e.g., Parkinson, Alzheimers, etc.) may be treated with electrical leads (wires) that extend deep into a patient's brain and stimulate a selected portion of the brain with electricity. Traditionally, the electrical leads extend through one or more burr hole, which are holes made in a patient's skull. The industry has found that simply extending leads through a burr hole makes it difficult to maintain the leads' proper position over time. As such, burr hole coverings were developed to cover open portions of the skull and assist in maintaining the leads' positions.

An example of a conventional burr hole covering is a burr hole plate. Burr hole plates are often thin, circular immobile plates having one or more holes therein. After a burr hole is drilled, the plate is placed on the skull such that one of the holes within the plate lines up with the burr hole. The distal portion of the lead is placed into the proper position within the brain and the proximal portion of the lead exits the burr hole and is strung through the hole of the plate prior to the plate being mounted to the skull. Thereafter, the skull plate is mounted to the skull around the burr hole via screws, and it is expected that the plate will hold the lead in position.

While the burr hole plate may help maintain the lead's position, the inadaptable design has left much to be desired. The hole within the plate is fixed during manufacturing, but unfortunately, surgery is an inexact and sometimes unpredictable procedure. Only after a surgeon has removed necessary portions of the patience's scalp, drilled one or more holes into the patience's skull, analyzed and determined an optimal lead diameter, and positioned the lead deep within the patient's brain, will the doctor be able to precisely determine whether the hole within the burr hole plate is of the optimal diameter and in the optimal position within the plate. At times, the determined optimal lead diameter proved to be too large to be supported by the burr hole plate and the optimal burr hole's position did not line up with a hole within the burr hole plate.

The industry has attempted to reduce the inadaptability of the burr hole plate design by designing the plate with holes that are oversized, thereby ensuring that the hole of the plate is able to accommodate the lead a surgeon decides to use. However, some surgeons decide to use leads that are thinner than the oversized hole, and ill-fitting holes cause the leads to shift over time and lose their optimal positioning. Substantial lead shifting necessitates additional procedures to correct the shift, which increases risk to patients, decreases effectiveness of the procedure, and increases costs for all. Further, oversized holes cause portions of the skull to remain exposed and unprotected. This is certainly a drawback considering covering open portions of the skull is one of the functions of the burr hole covering.

The industry also attempted to reduce inadaptability of the burr hole plates' design by designing the plate with several holes of various sizes that are located at various locations within the burr hole plate. This attempt to fix the problems of burr hole plates has led to more frustration. Referring back to the surgical example above, after having determined the size and placement of a lead, the determination may be thwarted by the burr hole plate when the hole of proper size is located at the wrong location within the plate. Again, the surgeon resorts to selecting a hole that is the closest match to the patient's needs, but ill-fitting holes cause leads to shift over time and lose their optimal positioning. As explained above, ill-fitting holes may cause additional surgeries and/or leave portions of the skull unprotected.

Further, the immobility of burr hole plates cause the installation to be tedious. During installation, after having positioned the lead deep within the brain, the surgeon threads the lead through the hole within the plate and thereafter must hold everything steady while drilling the plate into the skull. Holding steady the position of a lead, a plate, a drill, and screws all at the same time has been proven to be quite difficult. Often the position of one or more components is lost during the installation process, thereby causing the process to be started over.

In response, some in the industry have moved to a two component design, for example, a two component burr hole clamp system. Typically, a burr hole clamp system includes a hard anchor (e.g., titanium clamp) that clamps a soft inner sleeve (e.g., silicon plug). The anchor has an open state and a closed state. Further, the anchor includes a hole through which a lead may pass. The hole is larger in the open state and smaller in the closed state. During installation, a surgeon may drill a burr hole. Then, the distal end of a lead may be positioned deep within the brain, and the proximal end of the lead may be threaded through the soft inner sleeve of the system. Thereafter, the anchor, in its open state, is positioned around the soft inner sleeve at the burr hole. The anchor is transitioned to its closed state, wherein the anchor clamps the soft inner sleeve through which the lead is threaded. The soft inner sleeve functions similar to an o-ring gasket seal, which holds the lead steady, prevents shifting, and provides skull coverage even when the hole of the anchor is larger than a surgeon selected lead. After the anchor clamps the soft inner sleeve, the anchor is mounted to the skull via screws.

While the two component burr hole clamp system assists with the lead shifting problems described above, the design has left much to be desired. For instance, installation of the burr hole clamp system is even more tedious than burr hole plates. As explained, after having positioned the lead deep within the brain, the surgeon threads the lead through the soft inner sleeve, positions the anchor around the sleeve, and positions the anchor on the skull at the burr hole. Thereafter, the surgeon must hold everything steady while drilling the anchor into the skull. Holding steady the position of the lead, the soft inner sleeve, the anchor plate, the drill, and the screws all at the same time has been proven to add difficulty to installation of simple burr hole plates. Often the position of one or more components is lost during the installation process, thereby causing the process to be started over.

In an effort to reduce the complexity of burr hole clamp systems' installation, some in the industry designed an anchor that partially mounts to the skull before positioning the lead and the soft inner sleeve. The thought being, if the anchor is at least partially drilled into place, then one less component must be held steady during the final installation of the lead and soft inner sleeve. To achieve this goal, the anchor includes a hinged portion that provides the open and closed states of the anchor. During installation, the anchor is mounted to the skull around the burr hole via screws. The hinged portion of the anchor is not yet mounted to the skull. Then, after having positioned the lead deep within the brain, the surgeon threads the lead through the soft inner sleeve, positions the soft inner sleeve within the anchor, closes the hinged portion of the anchor, and mounts the hinged portion of the anchor to the skull via screws. The partial installation of the anchor prior to positioning the lead and soft inner sleeve reduces some of the installation complexity, but still leaves much to be desired.

Due to the two component design, a surgeon is still tasked with steading multiple component pieces in position while installing the final screws. Often the position of one or more components is lost during the installation process, thereby causing the process to be started over. Further, the soft inner sleeve typically extends into and out from the anchor. Patients complain that the burr hole clamp system is uncomfortably thick, which makes them unpopular. In embodiments, after a burr hole system is mounted to the skull, skin is grown over the anchor and soft inner sleeve to provide protection from infection and minimize the appearance of the implant. In sub-dermal systems, the thickness of the implant is of great importance because the location of the sub-dermal implant appears to be a deformity. The two tiered design of two component systems cause the burr hole covering to be significantly thicker than burr hole plates. Due to this thickness, a patience's apparent deformity is a source of great embarrassment and causes some patients to avoid the procedure despite its neurological benefits. Further, while most burr hole coverings are abrasive to the dermis and subcutaneous tissues, the increased thickness and complexity of two component systems cause them to be increasingly abrasive. Moreover, the soft inner sleeve causes increased thickness making it harder for patients to comfortably lay down and/or rest in high back seats (e.g., airplane seats). Further still, in order to ensure the proper sealing effect, the soft inner sleeve typically extends into the burr hole. Thus, the two component system causes abrasiveness and irritation above and below the skull. In short, two component burr hole plugs cause physical and emotional discomfort to patients.

In an effort to solve the problems caused by burr hole plates and two component burr hole clamp systems, some in the industry have moved to burr hole plugs. Burr hole plugs are typically a two component device having a plug base that mounts to the skull, and a retainer that maintains the lead's position. When installed, the retainer mounts into the plug base, which holds the retainer in place. The plug base is mounted to the skull using screws and has an aperture in its center. When mounted, the aperture is positioned such that the aperture exposes a burr hole therethrough. After mounting the plug base to the skull, a lead may extend through the aperture, into the burr hole, and be positioned into the brain. The size of the burr plug's aperture is purposefully bigger than any expected burr hole, and instead, is sized to receive the second component, a retainer, therein. The retainer is then installed by clamping the lead and being fitted (e.g., snapped into) into the aperture of the plug base. The burr plug holds steady the retainer, which in turn holds the lead in place.

This two component design of the burr hole plug reduces installation complexity; however, the design leaves much to be desired. As with the clamp system, the two component design makes manufacturing and packaging more complicated and expensive. Because the retainer must perfectly seat into the plug base to be held securely, the fitting components of the retainer and the fitting components of the plug base have to be manufactured with extreme precision. Minimal manufacturing error is sufficient to cause the device to fail. Further, since the two different components are manufactured using two different machines, manufacturing facilities have to develop techniques to ensure the proper retaining component is properly packaged with the proper plug base. Improper packaging leads to malfunctioning burr hole plugs being delivered to a surgical room, which can be costly to the patient, surgeon, and surgical facility alike.

Further still, the two component burr hole plugs are uncomfortably thick, which makes them unpopular with patients. Due to this thickness, a patient's apparent deformity is a source of great embarrassment and causes some patients to avoid the procedure despite its neurological benefits. Further, while all burr coverings are abrasive to the dermis and subcutaneous tissues, the increased thickness and complexity of burr hole plugs cause them to be increasingly abrasive. Moreover, burr hole plugs' increased thickness makes it harder for patients to comfortably lay down and/or rest in high back seats (e.g., airplane seats). In short, burr hole plugs cause physical and emotional discomfort to patients.

Further still, a problem common to burr hole plates, two component burr hole clamp systems, and burr hole plugs is lead projection. When a lead exits a fully installed burr hole cover, the space of the burr hole covering causes the lead to project out away from the skull. Moreover, the thicker the burr hole cover, the larger the lead projection. The lead projection causes the implant system to be even thicker, which as explained above, causes patient embarrassment and discomfort. In embodiments wherein the lead projection is sub-dermal, the lead projection causes additional lumps, abrasiveness, and irritation. In embodiments wherein the lead projects out of the skin at the burr hole covering, the lead projection runs the risk of being caught in something (e.g., a hair brush) and shifting from its precise position deep within the brain. In short, traditional burr hole cover systems have yet to provide a satisfactory solution to lead projection problems.

SUMMARY

The present application describes a lead stabilizer that may be surgically implanted sub-dermally on a patient's skull. The lead stabilizer may be a single component including at least a first portion and a second portion that are connected via a hinge. The first and second portions may transition, via the hinge, between an open and closed position. When installing the lead stabilizer, a user may install a lead deep within the brain, wherein the lead extends out of the skull. The user may open the lead stabilizer, position the lead stabilizer such that the lead is between the first and second portions, and close the lead stabilizer thereby clamping the lead therebetween. The lead stabilizer may also be affixed to the skull at the burr hole, wherein the lead stabilizer stabilizes the lead in place and prevents the lead from shifting.

The lead stabilizer may also include one or more surface channels that secures the lead therein. The surface channel may run along the surface of the lead stabilizer that is distal to the skull (e.g., the face of the lead stabilizer visible to the surgeon after implantation) and may be integral to the first portion and/or second portion of the lead stabilizer. A surface channel holds a lead flat against the distal surface of the lead stabilizer thereby reducing the lead's projection from the skull.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

DESCRIPTION OF DRAWINGS

For a more complete understanding, reference is now made to the following descriptions taken in conjunction with the accompanying drawings, in which.

Like reference symbols in the various drawings indicate like elements.

DETAILED DESCRIPTION

In accordance with aspects described in this application, an adaptable lead stabilizer is provided that stabilizes one or more leads of various sizes (e.g., unpredictable sizes) extending from one or more burr holes. Further, embodiments of lead stabilizers herein may comprise a single integral component, thereby reducing manufacturing and packaging costs, reducing the complexity of surgical installation, and reducing the thickness of the device. Further still, embodiments of lead stabilizers herein may include integral surface channels that secure leads extending from one or more burr holes, which reduces lead projection. As such, embodiments of lead stabilizers herein provide increased patient comfort and decreased embarrassment.

Figure 1:
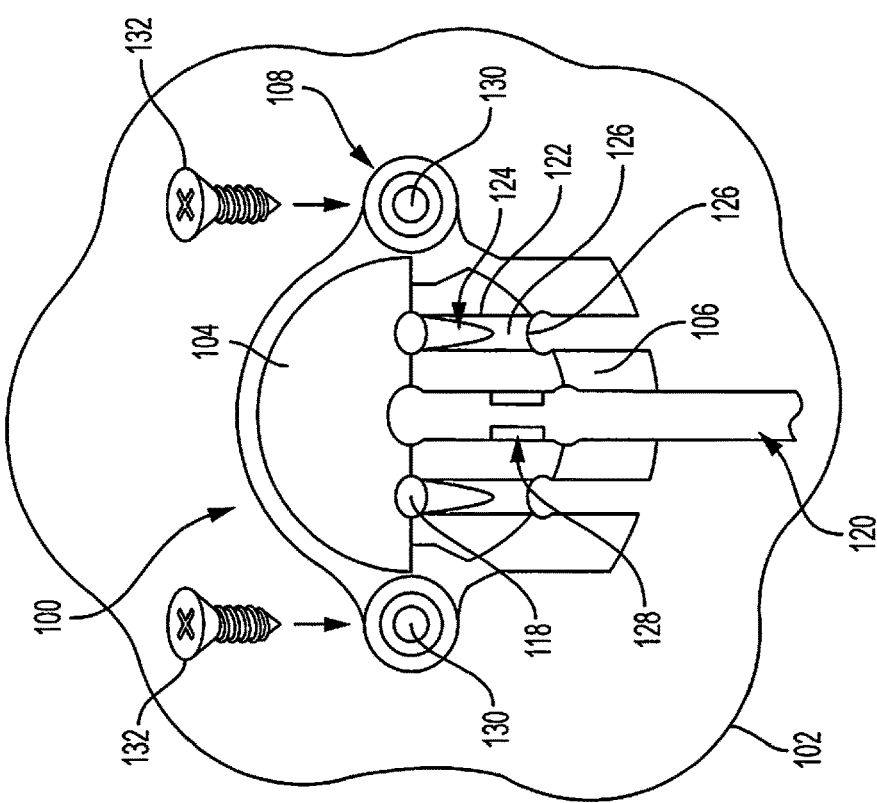
FIG. 1 is an example illustration of a lead stabilizer.

FIG. 1 is an example illustration of a lead stabilizer 100 as seen from outside a patient's skull 102. Lead stabilizer 100 may include a first portion 104 and a second portion 106 that come together to form a plate. If desired, lead stabilizer 100 may include additional portions (e.g., third portion, nth portion), which come together to form the plate. Lead stabilizer 100 includes one or more hinge 108 connecting first portion 104 and second portion 106 (and/or any additional portions). Lead stabilizer 100 articulates between an open position (shown e.g., in FIGS. 3 and 4) and a closed position (shown e.g., in FIGS. 1, 2, 5, and 6).

When in the closed position, the first portion 104 and second portion 106 come together to form a plate having one or more apertures 118. A lead 120 may extend out from a patient's brain, through a burr hole in the patient's skull 102, through aperture 118, and extend away from lead stabilizer 100. Lead 120 may be an electric lead, a coated wire having one or more electrodes at the proximal end (e.g., the end installed in the brain), an extension wire, a deep brain stimulator (DBS) lead, and/or the like. Lead 120 may be used to provide electrical pulses to a particular portion of the brain in order to treat brain syndromes and/or diseases (e.g., Parkinsons, Alzheimers, Dystonia, etc.).

The distal surface of lead stabilizer 100 may include one or more integral surface channels 122. The distal surface of lead stabilizer 100 is the surface facing away from the skull in the z direction, the outer surface of the lead stabilizer as seen from the surgeon's perspective after installation of lead stabilizer 100 as shown in FIG. 1, the outer surface of lead stimulator 100 that is approximately parallel to the outer surface of the skull. Surface channel 122 is an open faced channel (e.g., groove) that extends lengthwise on the surface of lead stabilizer 100. Surface channel 122 has a proximal end 124 that terminates at an aperture 118 and a distal end 126 that terminates the perimeter 128 of lead stabilizer 100.

In embodiments, first portion 104 may include one or more surface channel 122; second portion 106 may include one or more surface channel 122; and any additional portions (e.g., nth portion) may include one or more surface channel 122. In the example illustrated in FIG. 1, second portion 106 includes three surface channels 122 each having a proximal end terminating at three respective aperture 118.

The depth of a surface channel 122 may vary as surface channel 122 extends lengthwise to the distal end 126 at the perimeter 128 of lead stabilizer 100. As seen best in FIG. 2, example surface channel 122 is deepest at the point of termination at aperture 118. The proximal end 124 then slopes upward (e.g., the channel depth becomes more shallow) as surface channel 122 extends lengthwise towards the distal end 126. In embodiments, the depth of surface channel 122 slopes upward from the proximal end 124 for a first length. Then the depth of surface channel 122 maintains a substantially constant depth for a second length terminating at the distal end 126. Accordingly, the proximal end 124 of surface channel 122 may terminate at aperture 118 at a first angle, the distal end 126 of surface channel 122 may terminate at the perimeter 128 of second portion 106 at a second angle (e.g., 90 degrees), and the first angle is larger than the second angle.

The varying sloping depth of surface channel 122 allows lead 120, which is traveling in the z direction up and out of the skull, to curve out of aperture 118 at an obtuse angle and seat into surface channel 122. Such a transition from the burr hole, through aperture 118, to surface channel 122 causes a lead directional change that is less abrupt than forcing lead 120 to make a 90 degree turn as lead 120 transitions from the burr hole, through aperture 118, to surface channel 122. By reducing the abruptness of the lead's 120 directional change, lead projection at aperture 118 is reduced and the lead is protected from excessive bending force which may damage the lead.

Surface channel 122 retains lead 120 therein. In embodiments, surface channel 122 may be more narrow than a diameter of lead 120 thereby causing surface channel 122 to hold lead 120 snuggly therein. Additionally and/or alternatively, surface channel 122 may include one or more flanges 128 (e.g., edges, ridges, lips, snaps, clips, projections, rims, fasteners, claps, and/or the like) that snaps lead 120 within surface channel 122. Holding lead 120 tight to surface channel 122 reduces lead projection as lead 120 travels away from aperture 118 and assists in preventing lead shifts. Please note that while FIG. 4 does not show a surface channel, a surface channel may be included in any embodiment as is desired.

As illustrated, lead stabilizer 100 further includes one or more fixation aperture 130, which assists in fixing lead stabilizer 100 to the skull 102. Fixator hole 130 receives fixator 132 (e.g., a screw, nail, fastener, cement, and/or the like), therein, and fixator 132 couples lead stabilizer 100 to skull 102. Fixator aperture 130 may traverse one or more hinge 108, wherein fixator 132 immobilizes hinge 108 in a particular position when fixator 132 is installed into the skull 102. For example, a surgeon may use screw 132 to traverse hinge 108 and mount lead stabilizer 100 onto skull 102, wherein upon one or more screw 132 being tightened, hinge 108 can no longer open and close.

Figure 3:
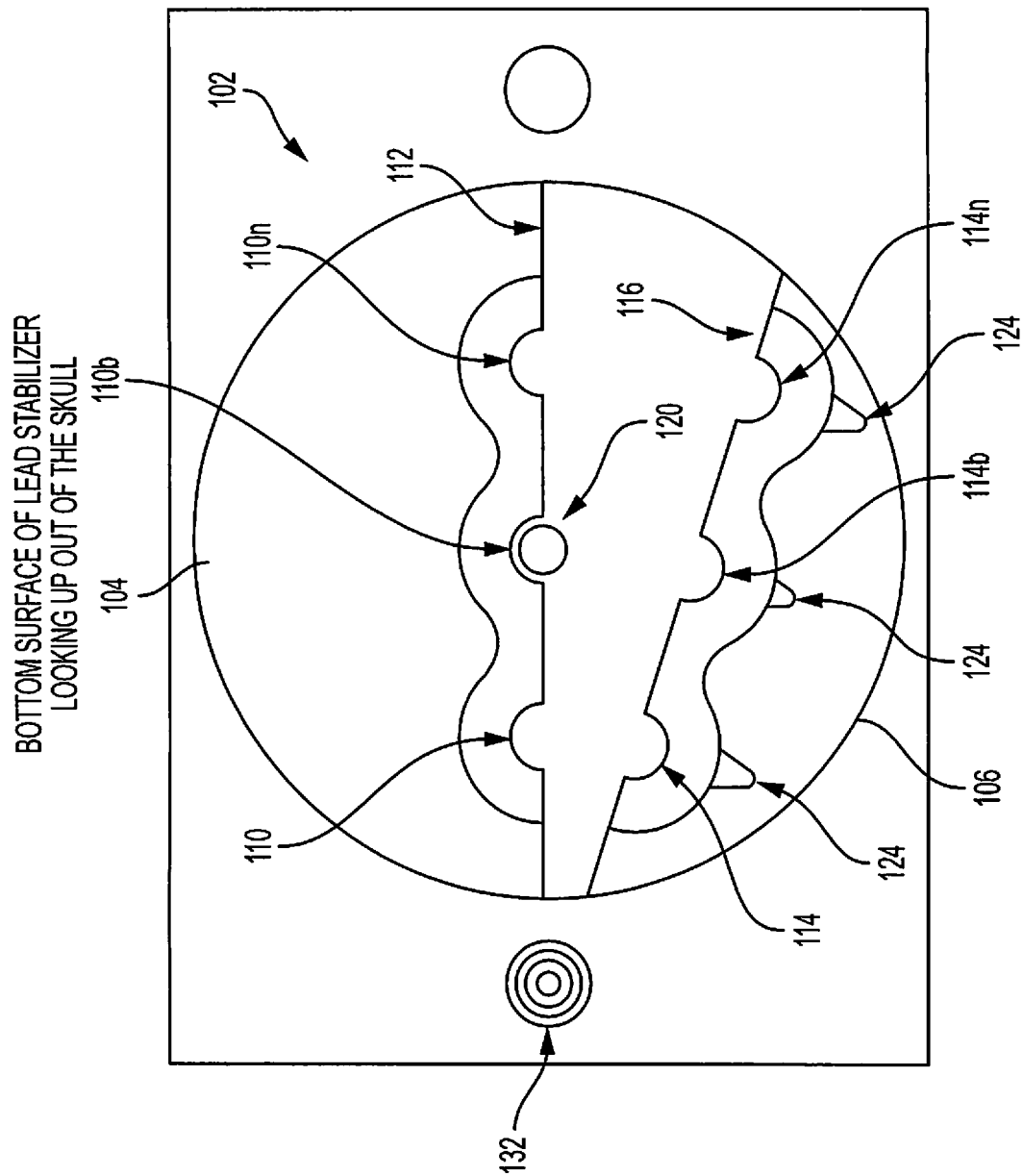
FIG. 3 is another example illustration of a lead stabilizer.

As explained, lead stabilizer 100 is used by a surgeon to stabilize one or more lead 120, which may be installed deep within a patient's brain. During the implantation procedure, a surgeon may prepare the site by removing and/or cutting back portions of the scalp covering the implantation site. Then, the surgeon may drill one or more burr holes in the patient's skull. Further, the surgeon may partially mount lead stabilizer 100 to skull 102. Lead stabilizer 100 may be transitioned into an open position at hinge 108 as shown in FIG. 3. In the open state, a portion of lead stabilizer 100 may be mounted to skull 102. For example, first portion 104 may be partially attached to skull 102 via one or more fixator 132, which traverses one or more fixator aperture 130. Fixator 132 may be tightened sufficiently to hold first portion 104 in position, but remain loose enough to allow one or more hinge 108 to pivot.

First portion 104 may be attached to skull 102 in a location such that a portion of a burr hole is surrounded by cutout 110 of first portion 104. As will be explained further below, cutout 110 will later meet together with a corresponding cutout 114 of second portion 106, thereby forming aperture 118. At some point (before or after first portion 104 is partially attached to skull 102), one or more leads 120 are selected for implantation within the brain. The length, thickness, and/or other characteristics of selected lead 120 may be selected based on the patient's needs at that time. After lead 120 is properly positioned within the brain and exiting the burr hole, hinge 108 is transitioned from an open position to a closed position thereby causing second portion 106 to clamp lead 120 in place.

Second portion 106 includes at least one cutout 114 at second portion's 106 inner edge 116. First portion 104 likewise includes at least one cutout 110 at first portion's 104 inner edge 112. While in the open position, cutout 110 and its corresponding cutout 114 move away from each other creating space therebetween. As such, even if a portion of lead stabilizer 100 is already partially attached to skull 102, this created space gives a surgeon room to perform other steps of the installation process (e.g., installing lead 120 within the brain, positioning its exit, drilling additional burr holes, and/or the like). Further, because a portion of lead stabilizer 100 is at least partially attached to skull 102, the procedure's complexity is reduced because lead stabilizer 100 is being held in place hands free. When the surgeon is ready, second portion 106 is transitioned to meet with first portion 104, such that cutout 110 and a corresponding cutout 114 form aperture 118 through which lead 120 extends. Many apertures 118 may be formed by a plurality of cutouts 110, 110b-110n meeting with a plurality of respective corresponding cutouts 114, 114b-114n.

Figure 5:
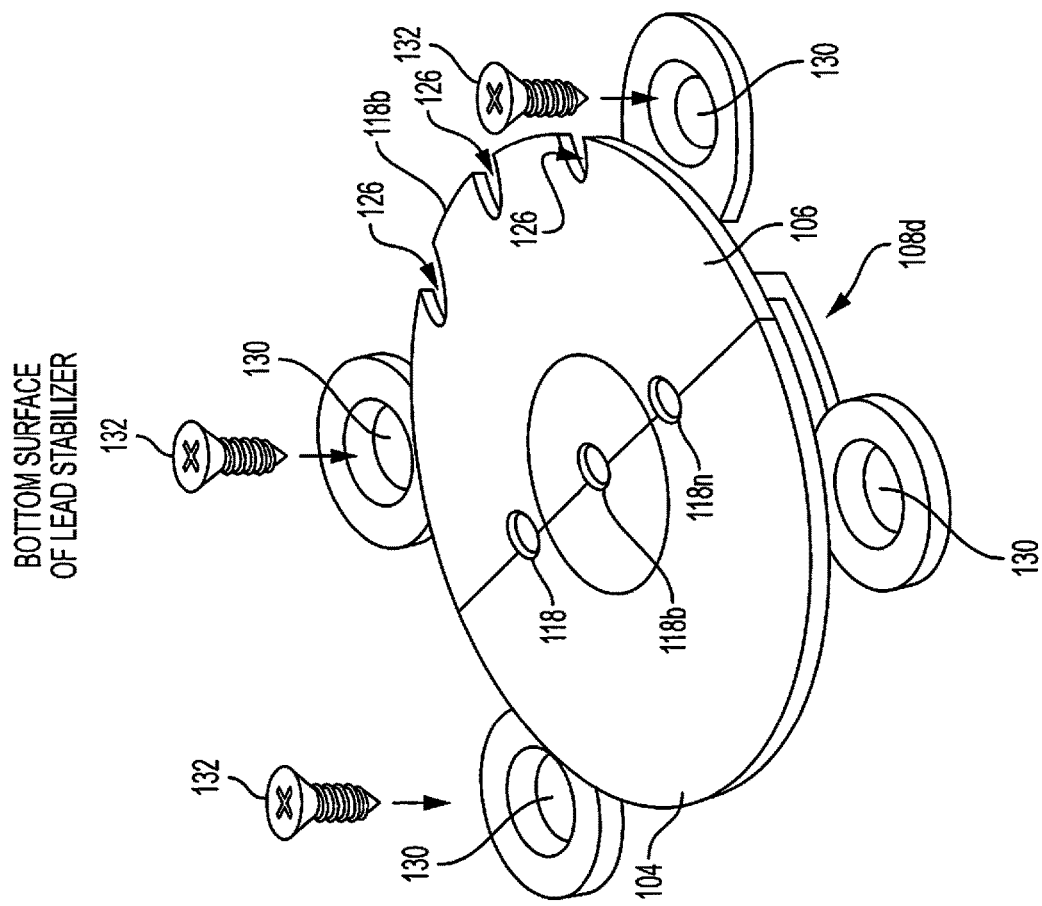
FIG. 5 is another example illustration of a lead stabilizer.

Once all leads 120 are implanted and lead stabilizer 100 is ready to be fully mounted, the surgeon may ensure that lead stabilizer 100 is in the desired position (e.g., closed position and/or a position between the opened and closed position) and then fully mount lead stabilizer 100 via additional fixators 132 through additional fixator apertures 130. FIGS. 1, 2, 3, and 4 show examples wherein lead stabilizers 100 have two fixator apertures 130. FIG. 5 shows an example lead stabilizer 100 having four fixator holes 130. Of course any number of fixator apertures 130 are contemplated.

Figure 2:
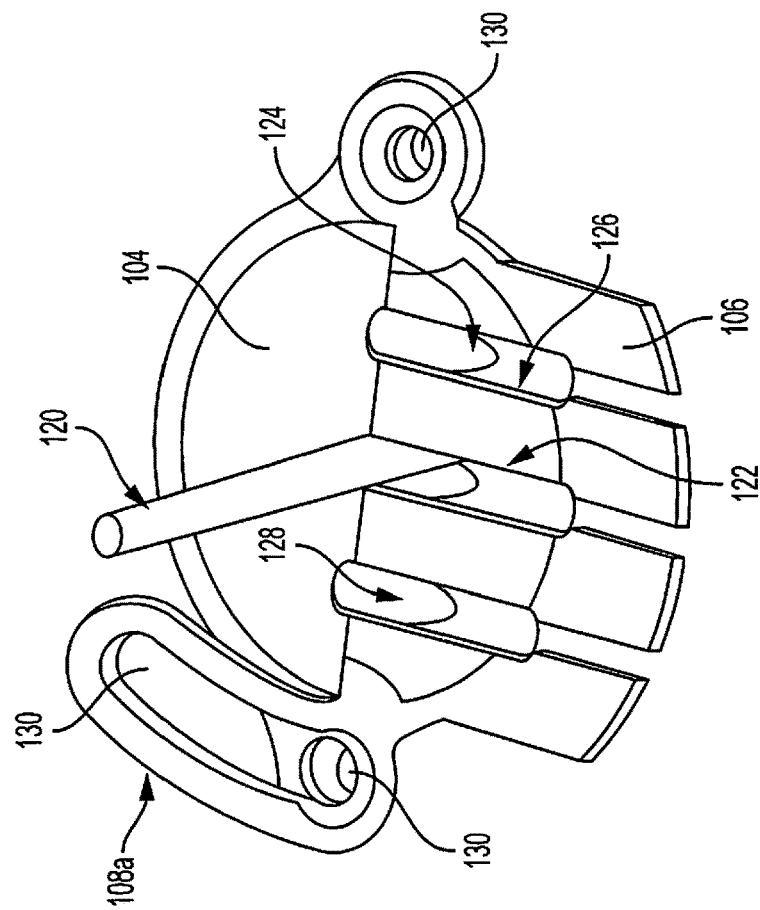
FIG. 2 is another example illustration of a lead stabilizer.
Figure 4:
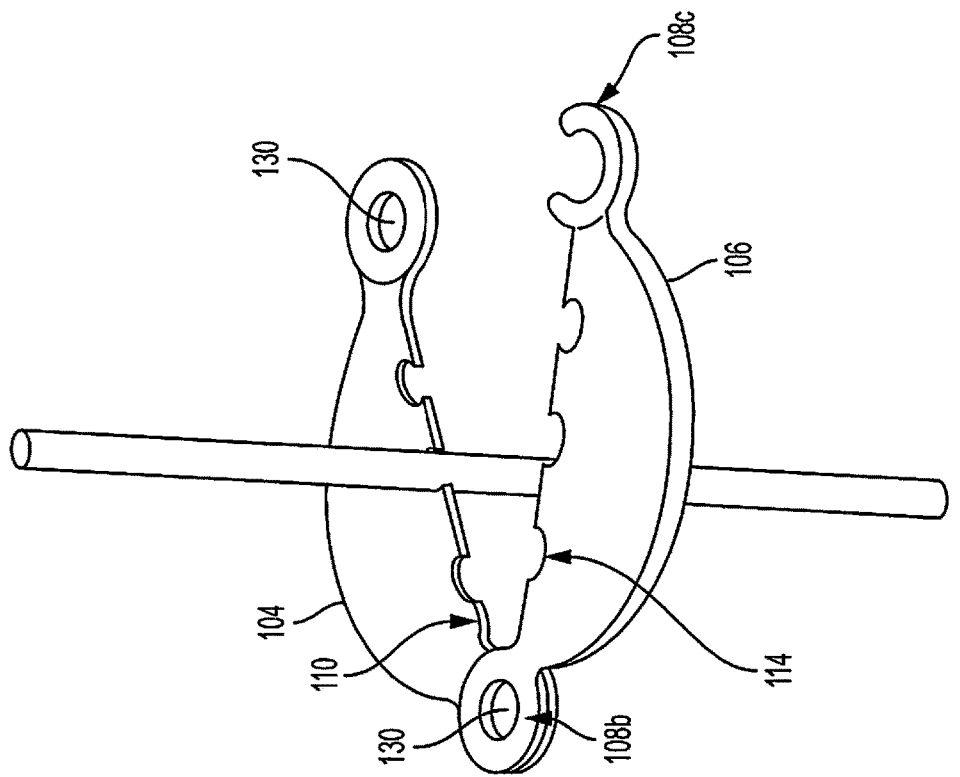
FIG. 4 is another example illustration of a lead stabilizer.

FIGS. 2, 4, and 5 illustrate a variety of hinges 108 that lead stabilizer 100 may include. FIG. 2 shows a slotted arm 108a, which allows second portion 106 to move laterally down away from first portion 104. In embodiments, slotted arm 108 of FIG. 2 may also allow second portion 106 to pivot away from first portion 104 at any point along the slotted arm. FIG. 4 shows an example of a lead stabilizer 100 having a plurality of hinges 108. Hinge 108 may be a break-away hinge 108 that functions as a hinge while joined with hinge counterparts (e.g., hinge 108b) but is also capable of breaking away from its hinge counterparts (e.g., 108c) when desired. In FIG. 4, lead stabilizer 100 may open from hinge 108b and/or hinge 108c, which makes lead stabilizer 100 more adaptable. From time to time, a surgeon may open hinge 108b, hinge 108c, and/or both hinges depending on circumstances encountered during a procedure. FIG. 5 shows an example hinge 108d, which is not traversed by a fixation hole 130.

Embodiments of lead stabilizers 100 may include one or more hinge 108 of one or more variety. Hinges 108 may also be immobilized in a variety of ways. In embodiments, hinge 108 may be immobilized by tightening a fixator 132, which penetrates fixation hole 130. For example, a surgeon may secure a screw 132 through hole 130 and into skull 102, which mounts lead stabilizer 100 to skull 102 while also immobilizing hinge 108. Various embodiments of hinges 108 may be immobilized by a pin, snap, cement, etc. Further, as shown in FIG. 5, hinge 108 is immobilized when first portion 104 and second portion 106 are mounted via fixators 132 traversing fixator apertures 130 into skull 102.

Figure 6:
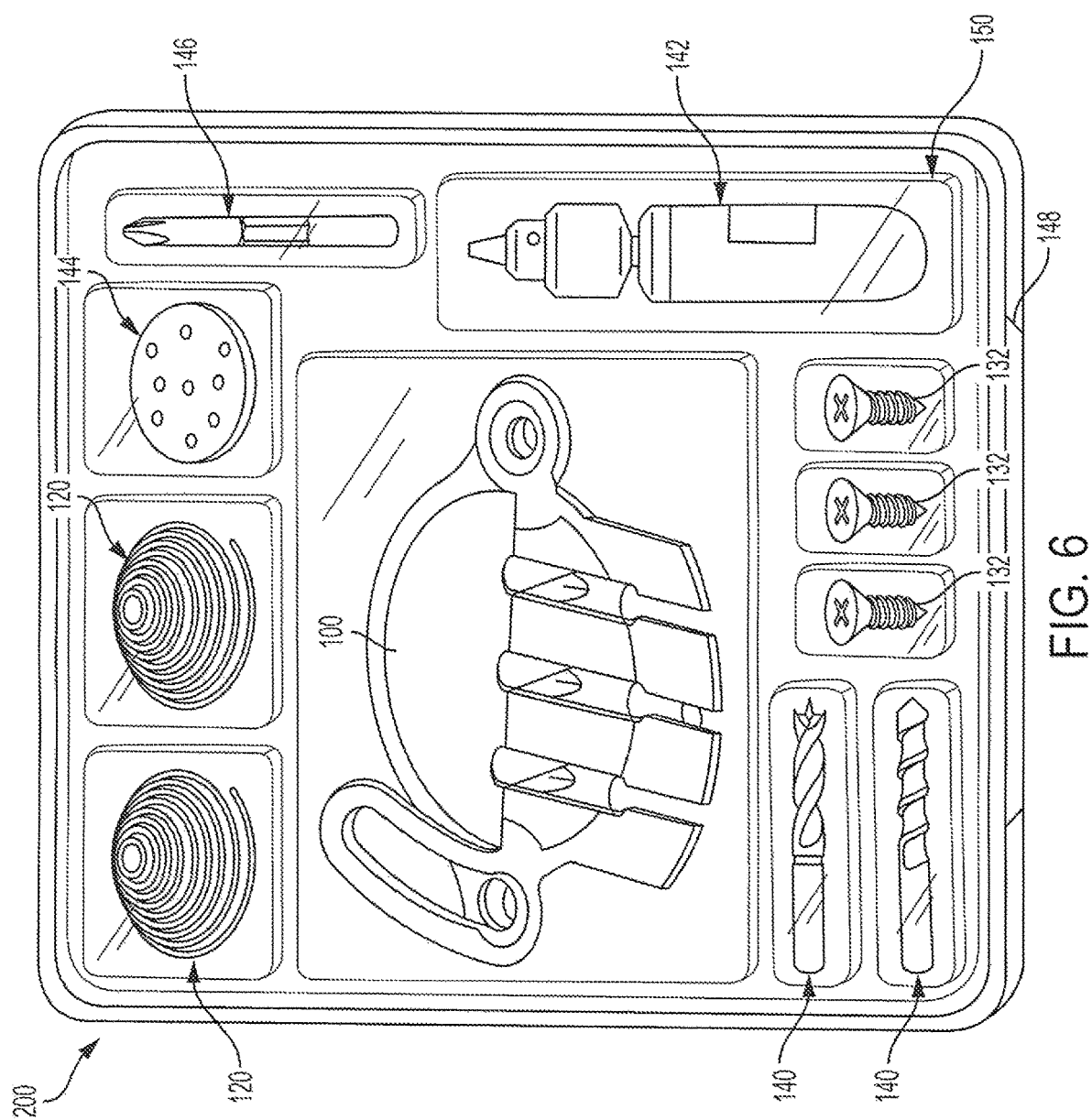
FIG. 6 is an example illustration of a deep brain stimulator surgical kit.

FIG. 6 is an example illustration of a deep brain stimulator (DBS) surgical kit 200. DBS surgical kit 200 may be manufactured, sterilized, and packaged at a manufacturing facility. Thereafter, the sterilized package may be delivered to a surgical facility and brought into a surgical room thereby reducing the preparation work of employees at the surgical facility. Further, prepackaging at the manufacturing plant reduces the likelihood of contamination of any individual components of the kit at least because less people handle the components at less facilities. Further still, prepacking the surgical kit may save the surgical facility money and time because equipment sterilizing devices and procedures may be avoided. Yet further, because the surgical kit comes prepackaged with the components used during the procedure, the surgical kit reduces the likelihood of an employee of the surgical facility forgetting to include one or more components on a surgical tray, which results in more efficient surgeries.

Example DBS surgical kit 200 includes one or more leads 120. Leads 120 may be of various thickness, length, impedance, coating material, electrode number, electrical conduit, texture, and/or other characteristics. Further, two or more leads 120 may have the same characteristics. Any number of leads 120 may be included in a surgical kit 200.

DBS surgical kit 200 may also include one or more lead stabilizer 100. Also included may be one or more fixators 132. Surgical kit 200 includes more screws 132 than will likely be used in the installation process. Providing extra screws is helpful just in case a screw is dropped during the procedure. A DBS surgical kit 200 may also include tools used during the implantation process. Example surgical kit 200 includes drill 142, which may be electrical or manual, and/or one or more drill bits 140 of the same or varying sizes. A surgeon may use drill 142 to make burr holes.

Further, the drill may be used to make holes which will receive fixators 132. In embodiments, one or more drill bit may be sized to correspond to thicknesses of leads 120 included in the kit; one or more drill bit may be sized to correspond to diameters of apertures 118 included in the kit; and one or more drill bit may be sized to correspond to diameters of fixators 132 included in the kit. Further, leads 120 of the kit may be sized to correspond to diameters of apertures 118 of the kit, which would improve lead stabilizer's grip of a lead. Further, fixators' diameters may be sized to correspond to apertures' diameters, which may reduce an amount of hardware included in the kit because drill bits for fixators would couple as drill bits for apertures.

DBS surgical kit 200 may also include one or more driving bit 146, which drive a fixator 132 into a skull 102. Examples of driving bits are phillips head bits, flathead bits, allen wrench bits, star head bits, and/or any other shape. A surgical kit may also include one or more sizing and guide instruments. Surgical kit 200 shows an example sizing wheel 144, which may be used to select one or more fixator and/or drill bit as well as be used as a stencil while drilling holes in skull 102. Any number and/or type of sizing instruments may be included which may assist a surgeon with cuts, holes, placement, etc. during the procedure.

In embodiments, some or all components of the kit are embedded in a well formed in tray 148. A well helps hold a component in place on the tray while the procedure is being performed. Tray 148 may be covered by cover 150, which may be transparent, translucent, and/or opaque. A transparent cover 150 may be helpful to see the components included within the kit. During assembly of surgical kit 200, each component included in a respective kit 200 may be sterilized. Then, tray 148 and the components held thereon are sealed with sterilized cover 150. Tray 148 and cover 150 create a sterile environment therein. As a result, sealed DBS surgical kit 200 may be transported and will maintain its sterility.

In embodiments, cover 148 may be sealed such that each individual component and/or some individual components are held in separate environments. For example, cover 150 may be a plastic cover that is sealed around each well. As such, a surgeon can unseal one well without unsealing another well. Thus, if a surgeon uses one lead 120, any unused leads 120 will remained sealed in their sterile environment and may be used at a later time.

It should be noted that DBS surgical kit 200 may be packaged at any facility including a surgical facility if desired.

While this specification contains many implementation details, these should not be construed as limitations on the scope of the invention or of what may be claimed, but rather as descriptions of features specific to particular implementations of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking may be advantageous.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

The invention claimed is:

1. A lead stabilizer that is surgically implanted on a skull, the lead stabilizer comprises:
   a first portion;
   a second portion;
   a hinge coupled to the first portion and the second portion, wherein the hinge includes a fixation aperture configured to receive a fixation device to affix the lead stabilizer to the skull, and wherein the hinge transitions the lead stabilizer between an open position and a closed position;
   a first cutout on an inner edge of the first portion;
   a second cutout on an inner edge of the second portion, wherein when the lead stabilizer is in the closed position, the first cutout and the second cutout frame an aperture through which a lead extends out from a burr hole;
   a surface channel that secures a portion of the lead extending out from the burr hole along an upper surface of the second portion, the surface channel comprising:
      a proximal end that begins at the aperture corresponding to the first and second cutouts, and
      a distal end that terminates at a perimeter of the second portion,
      wherein the surface channel has a depth that extends from the proximal end to the distal end.

2. The lead stabilizer of claim 1 wherein the depth of the surface channel is different at the respective proximal and distal ends.

3. The lead stabilizer of claim 1 wherein the surface channel is more narrow than a diameter of a lead retained in the surface channel.

4. The lead stabilizer of claim 1 further comprising:
   a plurality of first cutouts on the inner edge of the first portion;
   a plurality of corresponding cutouts on the inner edge of the second portion, wherein when the lead stabilizer is in the closed position, the plurality of first cutouts and the plurality of corresponding cutouts frame respective apertures.

5. The lead stabilizer of claim 4 further comprising a plurality of surface channels corresponding to the plurality of first and corresponding cutouts.

6. The lead stabilizer of claim 1 further comprising:
   one or more additional fixation aperture configured to receive another fixation device to affix the lead stabilizer to the skull.

7. The lead stabilizer of claim 1 wherein the hinge comprises:
   a slotted arm configured to allow the second portion to move laterally down away from the first portion.

8. The lead stabilizer of claim 1 wherein the lead stabilizer configured to be in the open position as the lead is installed.

9. The lead stabilizer of claim 1 wherein one of the first portion and the second portion is affixed to the skull before the lead stabilizer is in a closed position.

10. The lead stabilizer of claim 9 wherein the other of the first portion and the second portion is affixed to the skull after the lead stabilizer is in a closed position.

11. A Deep Brain Stimulator (DBS) surgical kit comprising:
   one or more sterile DBS leads;
   one or more sterile lead stabilizers, a lead stabilizer comprising:
      a first portion;
      a second portion;
      a hinge coupled to the first portion and the second portion, wherein the hinge includes a fixation aperture configured to receive a fixation device to affix the lead stabilizer to a skull and immobilize the hinge, and wherein the hinge transitions the lead stabilizer between an open position and a closed position;
      a first cutout on an inner edge of the first portion;
      a second cutout on an inner edge of the second portion, wherein when the lead stabilizer is in the closed position, the first cutout and the second cutout frame an aperture through which a lead extends out from a burr hole;
      a surface channel that secures a portion of the lead extending out from the burr hole along an upper surface of the second portion, the surface channel comprising:
         a proximal end that begins at the aperture framed by the first and second cutouts, and
         a distal end that terminates at a perimeter of the second portion,
         wherein the surface channel has a depth that is deeper at the proximal end as compared to the distal end; and
   one or more of the sterile fixators, which affix the lead stabilizer to the skull.

12. The DBS surgical kit of claim 11 wherein the lead stabilizer further comprises:
   a plurality of first cutouts on the inner edge of the first portion;
   a plurality of corresponding cutouts on the inner edge of the second portion, wherein when the lead stabilizer is in the closed position, the plurality of first cutouts and the plurality of corresponding cutouts frame respective apertures.

13. The DBS surgical kit of claim 12 wherein the lead stabilizer further comprising a plurality of surface channels corresponding to the respective apertures.

14. The DBS surgical kit of claim 11 wherein the lead stabilizer is configured to be in the open position as the lead is installed.

15. The DBS surgical kit of claim 11 wherein one of the first portion and the second portion is configured to be affixed to the skull before the lead stabilizer is in a closed position.

16. The DBS surgical kit of claim 15 wherein the other of the first portion and the second portion is configured to be affixed to the skull after the lead stabilizer is in a closed position.

17. The DBS surgical kit of claim 11 further comprising:
   one or more sterile burr hole drill bits that correspond to the aperture of the lead stabilizer.

18. The DBS surgical kit of claim 11 further comprising:
   one or more sterile drills that correspond to the one or more sterile burr hole drill bits.

19. The DBS surgical kit of claim 11 further comprising:
   one or more sterile sizing instruments.

20. The DBS surgical kit of claim 11 further comprising:
   one or more sterile trays upon which the one or more DBS leads, the one or more lead stabilizers, and the one or more fixators are stored.

21. A method of manufacturing a Deep Brain Stimulator (DBS) surgical kit comprising:
   providing one or more sterile tray that stores at least:
      one or more sterile DBS leads,
      one or more sterile lead stabilizers, a lead stabilizer comprising:
         a first portion;
         a second portion;
         a hinge coupled to the first portion and the second portion, wherein the hinge includes a fixation aperture configured to receive a sterile fixator to affix the lead stabilizer to a skull and immobilize the hinge, and wherein the hinge transitions the lead stabilizer between an open position and a closed position;
         a first cutout on an inner edge of the first portion;
         a second cutout on an inner edge of the second portion, wherein when the lead stabilizer is in the closed position, the first cutout and the second cutout frame an aperture through which a lead extends out from a burr hole;
         a surface channel that secures a portion of the lead extending out from the burr hole along an upper surface of the second portion, the surface channel comprising:
            a proximal end that begins at the aperture framed by the first and second cutout, and
            a distal end that terminates at a perimeter of the second portion,
            wherein the surface channel has a depth that is deeper at the proximal end as compared to the distal end, and
      one or more of the sterile fixators, which affix the lead stabilizer to the skull; and
   sealing a sterile cover on the one or more trays, wherein a tray and the sealed cover maintain a sterile environment therein.

* * * * *